United States Patent [19]

Kessler et al.

[11] Patent Number: 4,476,108

[45] Date of Patent: Oct. 9, 1984

[54] BACTERICIDAL METHOD

[76] Inventors: Jack H. Kessler, 202 W. Newell Ave., Rutherford, N.J. 07070; Robert S. Rosenbaum, 109 Anawan Ave., West Roxbury, Mass. 02132

[21] Appl. No.: 464,596

[22] Filed: Feb. 7, 1983

Related U.S. Application Data

[63] Continuation-in-part of Ser. No. 225,762, Jan. 16, 1981, abandoned.

[51] Int. Cl.³ .......................... A61K 7/28; A61K 7/20; A61K 37/48; A61K 33/40
[52] U.S. Cl. ........................................ 424/50; 424/53; 424/94; 424/130; 424/230; 424/258; 424/274; 424/317; 424/319; 424/330; 424/338; 435/78; 435/264
[58] Field of Search ...................... 424/50, 53, 94, 130, 424/230, 258, 274, 317, 319, 330, 338; 435/28, 264

[56] References Cited

U.S. PATENT DOCUMENTS

| | | | |
|---|---|---|---|
| 959,605 | 5/1910 | Queisser | 424/53 |
| 2,527,686 | 10/1950 | Sandberg | 424/58 |
| 2,554,464 | 5/1951 | Kraus et al. | 424/53 |
| 3,829,329 | 8/1974 | O'Driscoll et al. | 424/130 |
| 4,150,113 | 4/1979 | Hoogendoorn et al. | 424/50 |
| 4,154,815 | 5/1979 | Pader | 424/50 |
| 4,178,362 | 12/1979 | Hoogendoorn et al. | 424/50 |
| 4,269,822 | 5/1981 | Pellico et al. | 424/50 |

OTHER PUBLICATIONS

"Enzymes" by Dixon et al., Academic Press Inc., N.Y., 1958, pp. 100–104 and 208.
Elliott, K. A. C.: Oxidations Catalysed by Horseradish & Milk Peroxidases, Biochem. J. 26: 1281–1290, (1932).
Sizer, I. W. The Oxidative Inactivation of Poison Ivy Allergens by Peroxidase: J. of Invest. Dermatology 16, 103–110, (1951).
J. Clinical Periodon. 6, 115–130, (1979), Wennstrom et al.

*Primary Examiner*—Douglas W. Robinson

[57] ABSTRACT

The bactericidal method of the invention comprises forming a bactericide having a limited period of bacteriological activity with the bactericide including; a peroxide, a peroxidase and a source of donor molecules adapted to act as a substrate for said peroxidase; activating the bactericide to cause a catalyzed reaction by said peroxidase for generating free radicals from said source of donor molecules and simultaneously applying the bactericide for killing bacteria in the treatment of dental disease in situ such as in the oral cavity or as a denture cleaner.

8 Claims, 2 Drawing Figures

F I G. 2
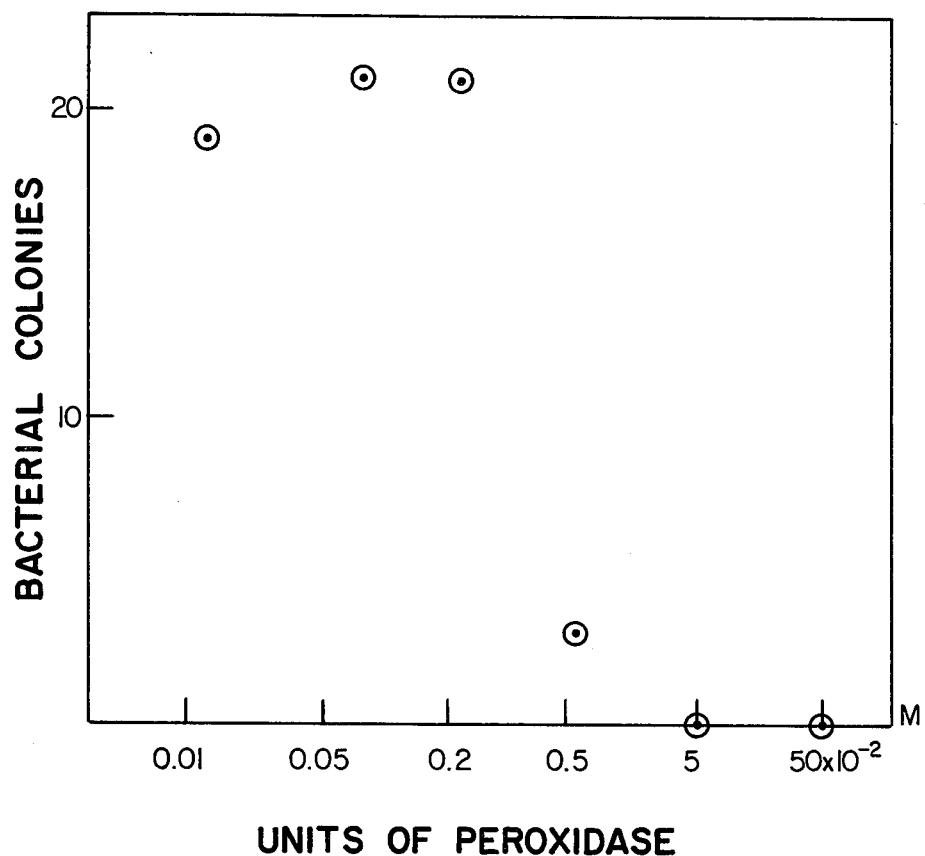

BACTERICIDAL METHOD

This is a continuation in part of application Ser. No. 225,762 filed on Jan. 16, 1981 and now abandoned.

BACKGROUND OF THE INVENTION

It has long been known that bacteria play a part in pathogenic dental caries. More recently an abundance of research has implicated bacteria as the causative agents of periodontal disease. Researchers have found a relationship between tooth deposits in periodontal disease. In 1965 a causal relationship was demonstrated between the daily accumulation of dental plaque which causes gingivitis. Others demonstrated in dogs that gingivitis if untreated progresses to periodontitis. Some different organisms are involved in gingivitis than those involved in periodontal disease. However, the organisms are in both cases various strains and types of bacteria.

To date, the art of treating caries, gingival and periodontal diseases is primarily surgical although some advances have been made in the control of disease by chemical means. Historically, the use of a toothbrush with dental floss has been recognized as a prevention and a treatment of the initial carious and gingival lesions. However, once the lesions progress beyond their initial stages surgical intervention is the treatment of choice. In the treatment of caries the lesion is excised using a rotating carbide steel or diamond burr mounted in a high speed handpiece. The cavity preparation is designed to accommodate a silver amalgam, gold or composite type of filling material which simulates the physiologic architecture of the tooth. In the treatment of periodontal diseases the goal of treatment is to remove tooth deposits with hand scalers and currettes and to surgically excise the periodontal pocket so the pocket is unavailable to foster growth of microorganisms.

Significant advances have been made in the field of preventative cariology through the employment of fluoride containing dentifrices and through the use of viscous polymers which are painted into the pits and fissures of the crown to obliterate these niches where routine oral hygiene practices are ineffective. The purpose of using fluoride as a nutritional supplement or as a topical agent is to incorporate fluoride into the hydroxyappetite crystalline structure of the enamel. This makes for a more symmetrical and perfect crystal structure which is more resistant to acid demineralization.

Plastic polymeric materials have been shown to be effective in preventing caries by painting them into pits and fissures soon after the eruption of each tooth into the oral cavity. This system works by etching the enamel surface with an acid to leech out surface enamel crystals and make a porous enamel surface. The viscous polymeric materials are painted onto the porous enamel surface and form an intimate mechanical bond with the enamel. Disadvantages of the polymer system include the necessary application of the material immediately after the eruption of the tooth, their propensity to dissolve and abraid and the cost of application.

The control of gingival and periodontal diseases via chemical means has had less success; although, many compounds both in literature and the patent have been proposed for inclusion in dentifrices or mouthwashes. At the present time several chemicals are being considered for their efficacy in preventing or treating periodontal diseases, but there is no accepted therapeutic which is universally recommended by the dental profession. Among such compounds considered for use are quarternary ammonium salts, ceramide peroxide, chlorhexidine, systemic and topical antibiotics, alexidine and other compounds having bactericidal efficacy. This approach recognizes that killing plaque bacteria controls caries, gingival and periodontal diseases.

The bactericidal properties of hydrogen peroxide are due to its dissociation into hydroxyl radicals which are toxic to bacteria. This property led long ago to consideration for its use in an oral dentifrice (U.S. Pat. No. 959,605, U.S. Pat. No. 975,814). However, The peroxide containing dentifrices of the prior art were not universally believed effective bactericides. Recent research has led to the proposal that the reason for their ineffectiveness was the slow dissociation of hydrogen peroxide into free radicals when contained in a typical composition. This dissociation is not rapid enough for a sufficient quantity of bactericidal free radicals to be generated during the application of the composition. An enzymatic method of generating hydrogen peroxide in situ (U.S. Pat. Nos. 4,150,113 and 4,178,362) attempted to overcome this problem by directing the formation of hydrogen peroxide to specific areas. However, this system does not appear to have gained widespread acceptance.

Hydrogen peroxide dissociates into free radicals; it is these free radical species which are known to be bacteriocidal. The rate at which free radical species are generated from the uncatalyzed decomposition of hydrogen peroxide determines the bacteriacidal efficacy of the compound. Enzyme catalyzed reactions are known to occur $10^{10}$ to $10^{15}$ times as rapidly as the corresponding non-enzymatic reaction. In accordance with the present invention an enzyme has been selected to catalyze the reduction of hydrogen peroxide for generating free radicals. The free radicals generated in this process are generated at greatly elevated rates relative to the free radicals generated from the non-enzymatic dissociation of peroxide.

Peroxidases are classified as enzymes which act on hydrogen peroxide as an acceptor of electrons. The different types of peroxidases are distinguished by the donor molecules from which they take electrons to donate to hydrogen peroxide. In accordance with the present invention a peroxidase is used to generate free radicals from donor molecules. The donor molecules must be capable of acting as a substrate for the peroxidase in generating such free radicals. The method of the present invention teaches how to control the generation of free radical species and the period of bacteriacidal activity. A bactericide is formed by combining three components, viz., a peroxide, a peroxidase and a source of donor molecules adapted to act as a substrate for the peroxidase. The bactericide will generate free radicals over a limited time period dependent upon the concentration level of each component and in particular the concentration level of the donor molecules and the peroxide since these components determine the duration of the catalyzed enzyme reaction in generating the free radicals. As long as this reaction continues there will be a supply of free radicals.

The concentration of donor molecules in the bactericide is of paramount importance since the donor molecules are transformed in the reaction into the bactericidal agents. The reaction of the donor molecules with the enzyme is the slowest step in the reaction mechanism. Accordingly the rate of generating free radicals and thus the efficiency of the bactericide is controlled by the quantity of donor molecules present. It has also been discovered in accordance with the present invention that a minimum concentration level of donor molecules exists below which the bactericide is ineffective for treating dental disease i.e., the rate of free radical production is too low to be characterized as having any noticeable bactericidal effectiveness. This minimum level for the donor molecules is at least $1.0 \times 10^{-5}$ molar which corresponds to 0.0001%. The minimum concentration level for the peroxidase, to achieve noticeable bactericidal effectiveness, is $0.38 \times 10^{-3}$ units per ml and for hydrogen peroxide the minimum concentration level, to achieve noticeable bactericidal effectiveness, is $1.33 \times 10^{-5}$ molar which corresponds to 0.00003%. In general the preparation used in the treatment of dental disease should have maximum concentration levels of about 0.1 milligram per ml for the enzyme, 1 milligram per ml for phenylalanine and 3% for hydrogen peroxide.

SUMMARY OF THE INVENTION

It is an object of this invention to provide a method for producing bactericidal free radicals in defined areas over a controlled time periods by applying a combination of a peroxidase, a peroxide and a source of donor molecules within predetermined concentration levels.

Still another object of this invention is to provide a method for hygenically treating humans for the dental diseases comprising dental caries, gingivitis and periodontal in the oral cavity.

Other objects and advantages will be apparent from the following detailed description of the invention when read in conjunction with the accompanying drawings for which:

FIG. 2 is a graph which demonstrates that the rate of free radical production can be controlled in accordance with the method of the present invention.

Figure 1:
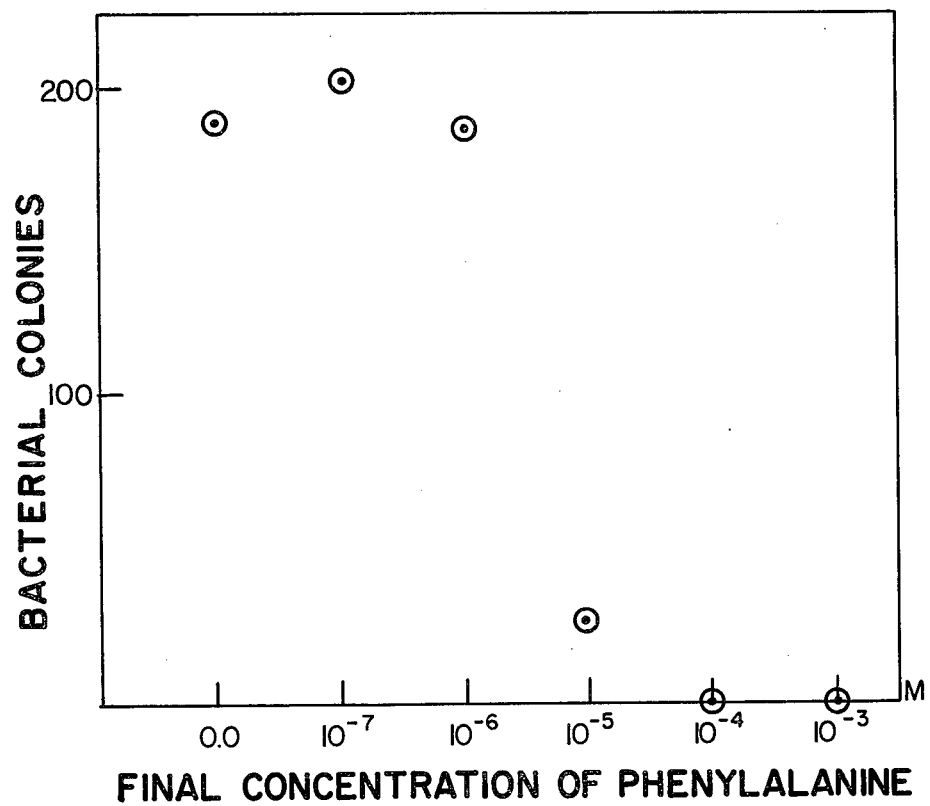
FIG. 1 is a graph showing the number of bacterial colonies present for different final concentrations of phenylalanine in Example 5.

According to the invention bactericidal free radicals are produced in a defined area in a short time period at an effective concentration by applying a combination of a peroxidase a peroxide and donor molecules in the defined area to rapidly and efficiently form bactericidal free radicals. Donor molecules are externally admixed with a peroxidase and peroxide to establish bactericidal action although in some cases, specific bacterial metabolites present may also supplement the action of the donor molecules. Preferably a carrier such as water is used although the admixture can be in various forms including paste, gels, powders and the like.

The method is preferably carried out to alleviate and treat bacterial diseases in the oral cavity as for example to aid in the prevention of dental caries, periodontal disease and gingivitis as well as the alleviation of periodontal disease and gingivitis alone or when coupled with other standard treating procedures in mammals and man.

A novel combination of this invention includes an admixture of a peroxidase and a peroxide along with a donor molecule in an amount to provide effective bactericidal free radical concentrations for use in the oral cavity without adversely affecting the oral cavity or causing harm thereto or for use as a denture cleaner.

The method of this invention is intended for use by humans in combination with any standard material, such as: toothpastes, mouthwash materials, tooth powder, chewing gum, prophylaxis paste, denture cleaner and the like. Because of the controlled bactericidal action provided by this invention and the rapid time period for production of these bactericidal free radicals, the invention is particularly effective to kill bacteria in the mouth in the treatment of various dental diseases. The method of this invention provides the capacity to kill oral microorganisms including those within plaque which are responsible for dental caries, gingival diseases and periodontal diseases. This invention differs from the prior art application of hydrogen peroxide to the mouth in that, unlike the prior art; rapid and efficient production of free radicals is provided in controlled concentrations high enough to provide bactericidal effectiveness in the mouth of the user without the necessity to use conditions or concentrations of peroxide which would be injurious to the users health.

DESCRIPTION OF THE PREFERRED EMBODIMENT

The material used as a bactericidal material in accordance with the method of this invention is a combination of donor molecules, a peroxide and a peroxidase which are capable of being transformed into bactericidal free radicals.

The admixture is preferably used in a carrier liquid or paste. Standard carriers can be used. In liquid form, water is the preferred carrier but any fluid nonreactive with the components of the admixture and compatible with the physiology of the mouth or other defined area in which the material is to be used, can be employed. For example, the carrier can be water, toothpaste of standard formulation, mouthwash of standard formulation, chewing gum, prophylaxis paste, denture cleaner, oral cleansing gels and the like.

The admixture can be used in a dry form after first lyophilizing the enzyme and using the salt of a peroxide. When this is done, all components can be mixed together and activated by introduction into the mouth or other defined area or first dissolving the material in a carrier such as water. When other than dry form materials are used and even in that case, it is preferred to use two part formulations. Standard containers such as toothpaste tubes having two compartments can be used. It is best to separate the peroxidase and the peroxide prior to introduction into the defined area to be treated since these materials will interact with each other particularly when in dispersed form in a carrier such as water.

The system of this invention incorporates the peroxide and an acceptor molecule. The enzyme peroxidase catalyzes transfer of electrons from donor molecules to acceptor molecules. When an electron is removed from the donor molecule, this molecule is transformed into a bactericidal free radical. A cycle of the enzyme mechanism is illustrated below:

| Step 1 | Enzyme  | + ROOH | OR Enzyme$_1$ | + H$_2$O |
| --- | --- | --- | --- | --- |
| Step 2 | OR Enzyme$_1$ | + AH$_1$ | OR Enzyme$_2$ | + A. |
| Step 3 | OR Enzyme$_2$ | + AH$_2$ | Enzyme | + A. + ROH |

Where R = CH$_3$, CH$_3$CH$_2$, H
AH = donor molecule
A. = free radical of donor molecule The increased rate of formation of radicals produced by this chemical system allows for rapid generation of high concentrations of bactericidal free radicals in defined areas of an oral cavity or other locations.

The peroxide in this invention is preferably hydrogen peroxide since it reacts rapidly and is relatively inexpensive. However, other peroxides can be used as for example methyl peroxide and ethyl peroxide. Other peroxides can be used although often the cost is increased and no added advantage is obtained.

The peroxidase used can be obtained from a wide variety of sources and is identified by the IUB and IUPAC, Enzyme Commission identification No. E.C. 1.11.1.7. Peroxidase, which uses a peroxide as an acceptor molecule, imparts to the bactericidal composition of this invention an enormous catalytic advantage in generating active constituents capable of killing selected bacteria in defined areas. A high concentration of free radicals are produced in short time periods for example, the reaction rate to form free radicals occurs essentially instantaneously and proceeds at a rate determined by the initial concentration of each of the three critical components of the system and the environment in which the reaction occurs. The peroxidase can come from a wide variety of sources and can be isolated by any of the well-known prior art procedures as used by several companies which offer a peroxidase for sale. The use of horseradish peroxidase is preferred since it is easily isolated, has low cost, and has very high stability giving it a long lifetime. Peroxidases have variable substrate specificities depending upon their source of isolation. Hydrogen peroxide is often the most effective substrate. However, methyl and ethyl peroxide are often acceptable and in some cases other peroxides can be used.

The donor molecules are organic molecules which can be acted upon to aid in formation of bactericidal free radicals. Many donor molecules can be used as will be recognized by those skilled in the art. In some cases the bacterial metabolites to be acted on as in the mouth can themselves form supplemental donor molecules when admixed with the system components used in this invention. The donor molecules for use in the present invention should have good stability with high reactivity. The following materials are particularly suitable: phenylethylamine, tyrosine, tryptophan, benzoic acid, salicylic acid, hydroquinone, dehydrophenylalanine, vanillan and para-aminobenzoic acid.

Different donor molecules have different abilities and reactivities and can be selected to focus bactericidal selectivity on any given preparation by careful selection of donor molecules or by designing specific donor molecules with high selectivity for specific bacteria.

A prerequisite for the storage of any preparation is not allowing all three components (donor molecules, acceptor molecules and peroxidase) of the system to combine under conditions where the catalytic process can occur. That is, it is imperative that the storage of the components will not allow the depletion of the component parts of the system until the reaction is initiated immediately prior to its use. If the components are allowed to react before intended for use, the combination of these components under such conditions will precipitate the depletion of the enzyme's substrate molecules and thereby attenuate the effectiveness of the preparation. Any combination of the components of this system (donor molecules, acceptor molecules or peroxidase) which precludes the catalytic reaction from occurring is acceptable for storage prior to use. That is, if it is practical to separate any one of the three components from the other two prior to administration, this would serve the purpose of preserving the integrity of the system. Alternately it is possible to have two separate mixtures which contain any two of the components of the system in any combination and to combine these two mixtures prior to use. This is acceptable so long as all three components will be present in the final composition under conditions which will allow the catalytic reaction to take place. Alternately, all three components of the system can be physically combined so long as they are unable to engage in the catalytic reaction with each other. That is, if all three components of the system are in powder form (sodium peroxide, donor molecule and lyophilized peroxidase) the three components of the system are physically admixed but are still incapable of meaningfully interacting with each other with respect to engaging in the catalytic reaction.

The activity of the peroxidase will usually be between $1 \times 10^{-4}$ and 0.1 units per cubic centimeter of the composition. By one unit of enzyme activity is meant that quantity of enzyme which will convert the conversion of 1 micromole of substrate (i.e. peroxide) per minute at 37 degrees C. PH 6.0 in 10 mM sodium phosphate.

The quantity of enzyme used can vary depending upon the specific formulation and its use but is preferably between $1 \times 10^{-3}$ and $1 \times 10^{-1}$ mg. of protein per cubic centimeter of the composition in which it was used.

EXAMPLE 1

A mouthwash was formed by admixture of the following:
Methyl Cellulose: 1.0% by weight of composition
Aromatic Flavoring: 1.0% by weight of composition
Tyrosine: 0.20% by weight of composition
Sodium Dodecyl Sulfate: 1.2% by weight of composition
Sodium peroxide: 0.1% by weight of composition
Sodium benzoate: 0.5% by weight of composition
Para-aminobenzoic acid: 0.40% by weight of composition
Distilled water: up to 100% by weight of composition.

To evaluate the effect this preparation has on a mixed population of human plaque bacteria, samples were collected from a patient's untreated periodontal pocket for subsequent studies. The plaque samples were diluted in prereduced anerobic solution, sonicated and plated on BMB media (Scott) which is a strict anerobic medium and incubated in a conventional anerobic jar. Plates 1 were streaked with the diluted and sonicated sample. Plates 2 contained the ingredients of the mouthwash except for peroxidase as well as streaked sample. Plates 3 contained all of the ingredients listed above including horseradish peroxidase mixed with the mouthwash in an amount of $1 \times 10^{-2}$ mg/ml as well as streaked sample. Plates were grown for five days at 37 degrees C and the number of colonies on each plate were counted at this time. The number of colonies for each of five trials are indicated below:

| Plate | Trial Number | | | | |
|---|---|---|---|---|---|
| | 1 | 2 | 3 | 4 | 5 |
| 1 | 40 | 48 | 32 | 26 | 55 |
| 2 | 7 | 2 | 8 | 13 | 6 |

-continued

| Plate | Trial Number | | | | |
|---|---|---|---|---|---|
| | 1 | 2 | 3 | 4 | 5 |
| 3 | 0 | 0 | 0 | 0 | 0 |

The results indicate that the complete formulations offer a substantial increase in bactericidal efficiency relative to the use of hydrogen peroxide.

EXAMPLE II

A toothpaste is formed having the following composition by weight of the composition:
Silica: 30%
Paraffin: 10%
Sorbitol (70% in water): 40%
Sodium Dodecyl Sulfate: 2.5%
Coloring substances, flavoring substances, sweetener, preservative: 2.4%
Sodium fluoride: 0.1%
Sodium bicarbonate: 5.0%
Hydrogen Peroxide: 10%.

Into a first chamber of toothpaste having the above composition was incorporated peroxidase in an amount of 50 units per cubic centimeter of the paste and into a second chamber containing the base paste was incorporated tyrosine in an amount of 0.20 milligrams per cubic centimeter of paste. When admixed and used as a toothpaste in the mouth, good bacteriocidal action is obtained.

When the toothpaste is stored at 37 degrees C for thirty days the enzyme activity declined from the initial level of 50 units per cubic centimeter to 42 units per cubic centimeter, indicating satisfactory stability.

EXAMPLE III

Following is the composition of another toothpaste falling within the invention.
Aluminum Hydroxide: 40% by weight of entire composition
Sorbitol: 30% by weight of entire composition
Sodium Dodecyl Sulfate: 2% by weight of entire composition
Sodium fluoride: 0.1% by weight of entire composition
Hydrogen Peroxide: 3% by weight of entire composition
Coloring substances, flavoring substances, sweetener, preservative: 2.5% of entire composition
Water: 22.4% by weight of entire composition.

Into chamber A of a toothpaste having the above composition was incorporated a peroxidase in an amount of 4.5 units per cubic centimeter of the paste and into chamber B was incorporated para-aminobenzoic acid in an amount of 0.25 grams per cubic centimeter of paste. When admixed as by placing equal amounts of chamber A contents and chamber B contents on a toothbrush and brushing, good bactericidal properties are found.

The peroxidase of toothpaste under number III does not lose any measurable activity after a period of 20 days at the storage temperature of 4 degrees C.

EXAMPLE IV

Saliva samples were vortexed and serially diluted 1/1000 into ¼ strength Ringers solution. 0.10 Ml of the 1/1000 dilution was inoculated with a sterile glass spreader over the surface of plates (Scott-Cat.#30-00-1200-Colombia Agar w/5% sheep blood) and grown for 48 hours at 37° C. The surface of the plate was scraped with a sterile loop and the bacteria were transferred to 10 ml of sterile water. This suspension was diluted 1/10,000 in sterile water. Thirty test tubes containing 0.20 ml of the diluted bacterial solution were mixed with 0.50 ml of 0.010 molar sodium phosphate, pH 7.0 containing the following components:

Series (A) phenylalanine—$1.0 \times 10^{-3}$ molar, $H_2O_2$—$1.33 \times 10^{-3}$ molar HRP Units Per ml (A) 0.38 0.038 0.0038 0.00038 ... $3.8 \times 10^{-11}$ Series (B) Enzyme Units $3.8 \times 10^{-2}$, $H_2O_2$ $1.33 \times 10^{-3}$ molar Phenylalanine Molarity (B) $1.0 \times 10^{-3}$ $1.0 \times 10^{-4}$ $1.0 \times 10^{-5}$ ... $1.0 \times 10^{-13}$ Series (C) Phenylalanine $1.0 \times 10^{-3}$, enzyme units $3.8 \times 10^{-2}$ molar Hydrogen Peroxide Molarity (C) $1.33 \times 10^{-1}$ $1.33 \times 10^{-2}$ $1.33 \times 10^{-3}$ ... $1.33 \times 10^{-11}$ These solutions were allowed to incubate for two minutes and each tube was vortexed before being plated out and grown for two days at 37° C. Series A did not exhibit any bacterial growth above a level of $3.8 \times 10^{-4}$ units of enzyme. Series B exhibited bacterial growth at concentrations of phenylalanine of $1.0 \times 10^{-5}$ molar and below. Series C did not display any bacterial growth at hydrogen peroxide concentrations of $1.33 \times 10^{-6}$ and above.

This experiment demonstrates that all three components of our system are necessary for the reaction to occur. In addition, the rate at which free radicals are generated can be controlled by adjusting any one of the components of the system. The time during which bacteriacidal entities are generated can likewise be controlled by adjusting the concentration of enzyme used in the preparation.

EXAMPLE V

Saliva samples were vortexed and serially diluted 1/1000 into ¼ strength Ringers solution. 0.10 Ml of the 1/1000 dilution was inoculated with a sterile glass spreader over the surface of plates (Scott-Cat.#30-00-1200) and grown for 2 days at 37° C. The surface of the plate was scraped with a sterile loop and the bacteria were transferred to 5 ml of sterile water. A one-thousandfold dilution of this suspension was made in 0.010 molar sodium phosphate, pH 7.0, and 1 ml was transferred to 6 different test tubes. Each of these test tubes contained 0.050 units of horseradish peroxidase and $1.0 \times 10^{-9}$ moles of hydrogen peroxide. Solutions of different phenylalanine concentrations were added to these test tubes to bring their final volume to 1.5 ml. These tubes were allowed to incubate for 2 minutes and then plated out on sheep blood-agar plates overnight at 37° C. The results of this experiment are shown in Graph 1 which demonstrates that it is possible to kill some percentage of a given bacterial population with this system.

EXAMPLE VI

Saliva samples were vortexed and serially diluted in ¼ strength Ringers solution. 0.10 Ml of the 1/1000 dilution was inoculated with a sterile glass spreader over the surface of plates (Scott-Cat.#3000-1200) and grown for 2 days at 37° C. A sterile loop was scraped over the surface of the plates and these bacteria were suspended in 10 ml of sterile water, vortexed and serially diluted 1/10,000 in sterile water. 0.50 Ml of this suspension was added to 0.50 ml of sodium phosphate (pH 7.0) containing $1 \times 10^{-4}$ molar phenylalanine and $1 \times 10^{-4}$ molar hydrogen peroxide. One hundred microliters of HRP at different concentrations were added to six of these test tubes and allowed to incubate for 15 seconds before being plated out on sheep blood-agar plates. The results are shown on Graph 2 which demonstrates that the rate of free radical production can be controlled by varying the components of the system.

While specific embodiments have been shown and described, many variations are possible. In all cases, where the materials are to be used in the oral cavity, they are compatible with the body and do not cause unwanted destruction to the body. For example the pH is such that it will not change the pH of the mouth out of a range of about from 6.7 to 7.4. The material is non-toxic to man and animals. Standard stabilizers, colorants, carriers and the like can be used.

Common ingredients of toothpaste to which the bactericidal compositions of this invention can be added include bases in amounts of from 10 to 50% by weight, colorants in amounts of from 1 to 2% by weight, fragrances or flavorants in amounts of 1 to 2% by weight and stabilizers in amounts of less than 1% by weight.

Suitable bases include sorbitol, glycerin, cellulose gum and carrageen. Suitable abrasives include silica, alumina, hydroxide, sodium silicate, sodium metaphosphate and magnesium aluminum silicate. Suitable colorants include titanium dioxide, FD & C Blue No. 1, FD & C Yellow No. 10. Suitable fragrances include spearmint, peppermint, lime, mint, sodium saccharin. Stabilizers include sodium benzoate. Many equivalent ingredients can be used.

Preferably mixtures of the present invention are made just prior to addition to the defined area where the bactericidal effect is to take place. Such admixtures preferably have from $1.0 \times 10^{-4}$ to $1.0 \times 10^{-1}$ units per cubic centimeter of a peroxidase, 0.00003 to 3% by weight of peroxide and 0.0001 to 10% by weight of a donor molecule when used. This combination can be further admixed with other formulas such as toothpaste, tooth powder, gels and the like where the amount of the combination in the overall formulation can vary greatly. Thus the carrier for the formulation can be water or other liquids or pastes. For use as a denture cleaner the maximum peroxide concentration should be 10% by weight.

We claim:

1. A method for hygenically treating humans for the dental diseases comprising caries, gingivitis and periodontitis in the oral cavity which comprises: forming a bactericide having a limited period of bacteriological activity; said bactericide comprising a peroxide selected from the group consisting of hydrogen peroxide, sodium peroxide, methyl peroxide and ethyl peroxide in a concentration range from 0.00003 to 3% by weight, a peroxidase within the classification E.C. 1.11.1.7 in a concentration range from $1.0 \times 10^{-4}$ to $1.0 \times 10^{-1}$ units per cubic centimeter and a source of predetermined donor molecules adapted to act as a substrate for said peroxidase, with the concentration of said donor molecules being in a range from 0.0001% to 10% by weight storing said three components in a nonreacting state; interacting the three components to cause a catalyzed reaction by said peroxidase for generating free radicals from said source of donor molecules and substantially simultaneously applying the three interacting components as an admixture to any desired location within the oral cavity whereby bacteria present at said location during said limited period of bacteriological activity will be killed.

2. A method as defined in claim 1 wherein said donor molecules is selected from the group consisting of: phenylethylamine, tyrosine, tryptophan, benzoic acid, salicyclic acid, hydroquinone, dehydrophenylalanine, vanillin and para-aminobenzoic acid.

3. A method as claimed in claim 2 wherein said peroxidase is horseradish peroxidase.

4. A method for hygenically treating humans for the dental diseases comprising caries, gingivitis and periodontitis in the oral cavity which comprises: forming a bactericide having a limited period of bacteriological activity; said bactericide comprising an admixture of at least three components each of which is in a dry form consisting of a peroxide selected from the group consisting of hydrogen peroxide, sodium peroxide, methyl peroxide and ethyl peroxide in a concentration range from 0.0003 to 3% by weight, a peroxidase within the classification E.C. 1.11.1.7 in a concentration range from $1.0 \times 10^{-4}$ to $1.0 \times 10^{-1}$ units per cubic centimeter and a predetermined source of donor molecules adapted to act as a substrate for said peroxidase with the concentration of said donor molecules being in a range from 0.0001% to 10% by weight, dissolving the admixture prior to administration in a liquid carrier solvent for activating said bactericide so as to cause a catalyzed reaction by said peroxidase for generating free radicals from said source of donor molecules and substantially simultaneously applying said admixture at any desired location in the oral cavity whereby bacteria present at said location during said limited period of bacteriological activity will be killed.

5. A method as defined in claim 4 wherein said donor molecules is selected from the group consisting of: phenylethylamine, tyrosine, tryptophan, benzoic acid, salicyclic acid, hydroquinone, dehydrophenylalanine, vanillin and para-aminobenzoic acid.

6. A method as defined in claim 5 wherein said peroxidase is horseradish peroxidase.

7. A bactericidal method for disinfecting a denture comprising forming a bactericide having a limited period of bacteriological activity; said bactericide comprising a peroxide selected from the group consisting of hydrogen peroxide, sodium peroxide, methyl peroxide and ethyl peroxide having a minimum concentration of 0.0003% by weight; a peroxidase within the classification E.C. 1.11.1.7 having a minimum concentration of $1.0 \times 10^{-4}$ units per cubic centimeter and a source of predetermined donor molecules adapted to act as a substrate for said peroxidase in a minimum concentration of 0.0001% by weight, storing said three components in a nonreacting state; interacting the three components to cause a catalyzed reaction by said peroxidase for generating free radicals from said source of donor molecules and substantially simultaneously introducing the three interacting components as an admixture into a liquid carrier solvent containing the denture whereby bacteria present in said denture during said limited period of bacteriological activity will be killed.

8. A method as defined in claim 7 wherein said donor molecules is selected from the group consisting of: phenylethylamine, tyrosine, tryptophan, benzoic acid, salicyclic acid, hydroquinone, dehydrophenylalamine, vanillin and para-aminobenzoic acid.

* * * * *